United States Patent

Niethammer

(10) Patent No.: US 8,623,006 B2
(45) Date of Patent: Jan. 7, 2014

(54) ACTUATION SYSTEM

(75) Inventor: Matthias Niethammer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 774 days.

(21) Appl. No.: 12/585,603

(22) Filed: Sep. 18, 2009

(65) Prior Publication Data

US 2010/0100089 A1    Apr. 22, 2010

(30) Foreign Application Priority Data

Sep. 24, 2008 (DE) .......................... 10 2008 048 686

(51) Int. Cl.
*A61B 18/18* (2006.01)

(52) U.S. Cl.
USPC .............................................. 606/34; 606/38

(58) Field of Classification Search
USPC ...................................................... 606/34, 38
See application file for complete search history.

(56) References Cited

U.S. PATENT DOCUMENTS

| | | | | |
|---|---|---|---|---|
| 5,891,131 | A * | 4/1999 | Rajan et al. | 606/5 |
| 6,478,793 | B1 * | 11/2002 | Cosman et al. | 606/34 |
| 6,524,308 | B1 * | 2/2003 | Muller et al. | 606/49 |
| 7,081,111 | B2 | 7/2006 | Boldstad | |
| 2003/0000535 | A1 * | 1/2003 | Galloway et al. | 128/898 |
| 2003/0097130 | A1 | 5/2003 | Muller et al. | |
| 2007/0073905 | A1 * | 3/2007 | Cynthia et al. | 710/1 |
| 2008/0039830 | A1 * | 2/2008 | Munger et al. | 606/33 |
| 2009/0105579 | A1 * | 4/2009 | Garibaldi | 600/409 |
| 2009/0221999 | A1 * | 9/2009 | Shahidi | 606/33 |
| 2010/0063496 | A1 * | 3/2010 | Trovato et al. | 606/34 |

FOREIGN PATENT DOCUMENTS

| | | |
|---|---|---|
| EP | 1009306 B1 | 4/2004 |
| WO | WO 2008090484 A2 | 7/2008 |

* cited by examiner

*Primary Examiner* — Linda Dvorak
*Assistant Examiner* — Jocelyn D Ram
(74) *Attorney, Agent, or Firm* — Harness, Dickey & Pierce, P.L.C.

(57) ABSTRACT

An actuation system is disclosed for actuating an ablation instrument for an ablation process in a tissue volume. In at least one embodiment, the actuation system includes: an input interface for image data of the tissue volume; an identification unit for identifying a target tissue using the image data; a model production unit for producing process models and/or refined fine process models of expected ablation developments, which is linked to a value derivation unit for deriving model measured values from a process model and/or to a value determination unit for determining measured values representing the ablation progress; a command derivation unit for deriving control commands on the basis of process models and/or for deriving refined control commands on the basis of fine process models; a comparator for comparing measured values and an instrument interface for transmitting control commands and/or refined control commands to the ablation instrument. In at least one embodiment, the invention also relates to an actuation method.

11 Claims, 3 Drawing Sheets

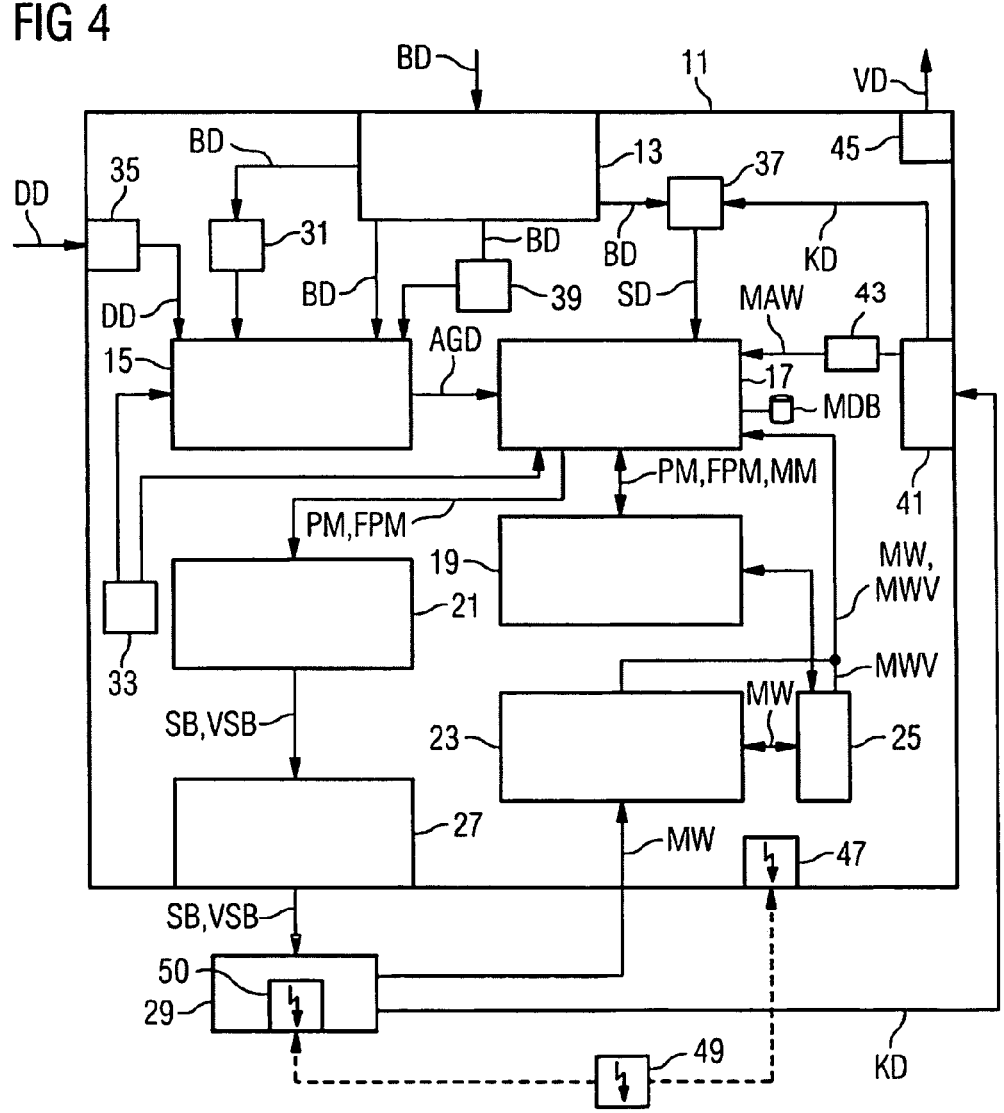

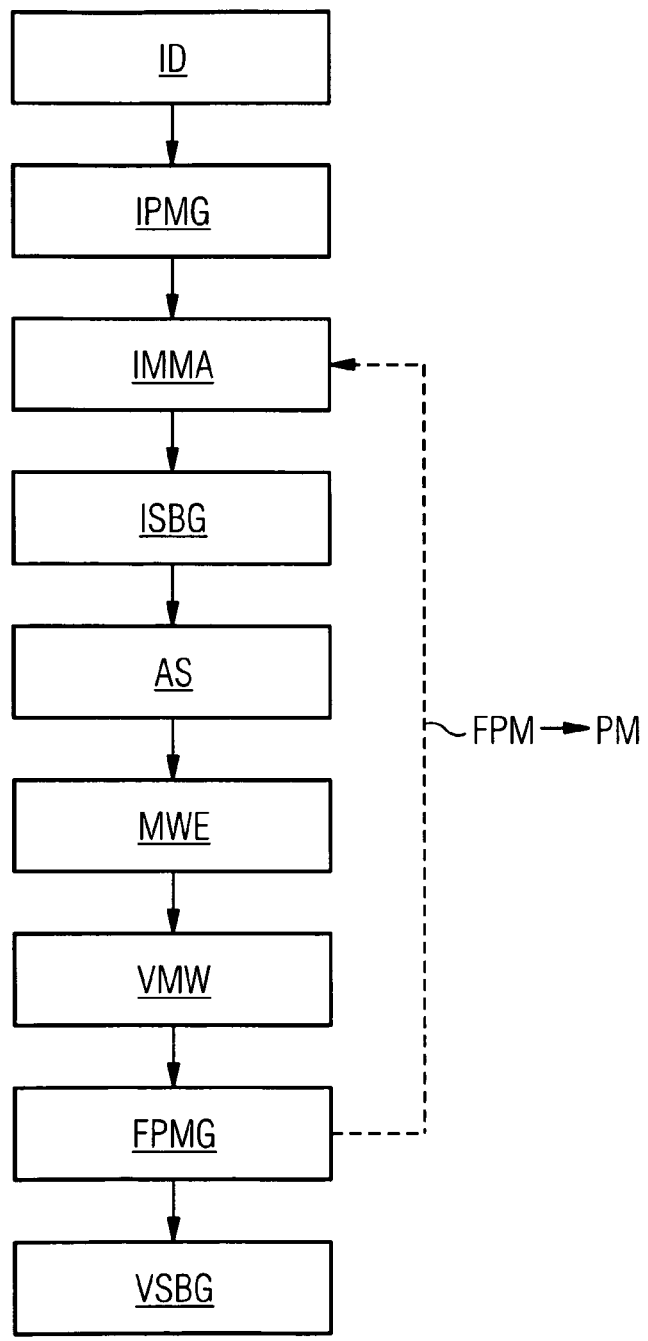

ACTUATION SYSTEM

PRIORITY STATEMENT

The present application hereby claims priority under 35 U.S.C. §119 on German patent application number DE 10 2008 048 686.8 filed Sep. 24, 2008, the entire contents of which are hereby incorporated herein by reference.

FIELD

At least one embodiment of the present invention generally relates to an actuation system for actuating an ablation instrument for an ablation process in a tissue volume. At least one embodiment also generally relates to an actuation method for such an actuation.

BACKGROUND

Ablation methods within tissue volumes are additionally supported these days by imaging systems, e.g. computed tomography scanners, magnetic resonance imaging scanners, ultrasound equipment or imaging systems based on similar imaging methods. Using the image data obtained therewith, ablation instruments can be navigated to a certain target within a tissue volume.

There are different ablation methods which all have in common that an instrument is positioned in the target tissue volume in order to destroy the tissue at the location: In the case of so-called cryoablation, this is performed by icing. The advantage of this method is that the icing zone is very recognizable in a computed tomography image. A very new method utilizes the effect of electroporation. Here, the cell membranes are changed by applying a very high, pulsed DC voltage and this leads to the death of the cell. The most frequently utilized method is RF (radiofrequency) ablation, in which radiofrequency waves are used to place thermal energy into the target tissue volume—that is to say the tumor is "cooked". In an exemplary manner, this method will be discussed in more detail below.

In the case of RF tumor ablation, a needle-shaped applicator is inserted into a tissue and pushed to the location of a tumor under monitoring on the basis of the image data from computed tomography. Once the applicator is in the target area, thermal energy is produced by microwaves and leads to the destruction of the tumor tissue.

There are different types of RF probes, with, in principle, it being possible to distinguish between needle-shaped probes and umbrella probes. In the case of umbrella probes, a number of individual antennas are deployed after positioning. They thus attain a larger ablation volume than the needle probes. In the case of needle-shaped probes, a plurality of probes ("cluster") are often used simultaneously in order to attain a certain volume.

During an ablation process, a temperature sensor installed in the respective probe or an impedance measurement determines when the end of the ablation has approximately been reached: In the case of an impedance measurement, an increase in the impedance, the so-called "roll-off", can be determined toward the end of the ablation. The roll-off is created when the corresponding tissue has been ablated and the conductivity decreases. It is usual to go through approximately two roll-offs before the ablation is finished. There can be an analogous process in the case of the temperature measurement too, with a temperature threshold being exceeded signifying the end of the ablation in this case.

In addition to the type of applicator, the extent of the ablated area depends inter alia on the application duration and the applicator power. The corresponding parameters are set in advance by a user on the ablation instrument as a function of different basic information. The basic information takes account of, for example, the size and extent of the respective tissue to be ablated, the type of tissue, vessels lying in the vicinity which could dissipate the heat and particularly sensitive zones such as nerves which shall not be adversely affected.

The product information by applicator producers often contains tables which reproduce the thermal expansion as a function of the instrument setting. These tables were determined on dead tissue and cannot go into the individual ablation situation. It is for this reason that they are not sufficiently accurate.

Hence, the most common method for setting the parameters currently is that a user works on the basis of his own experience. Naturally this still results in a high uncertainty in tissue ablations and, additionally, decisively depends on the experience of the respective user. This holds true in particular if the tissue volume to be ablated exceeds a diameter of 5 cm. In that case it can be expected that for example not all tumor cells of an affected tissue are acquired by the ablation. Therefore, in general, only tumors with a diameter of up to at most 5 cm are currently ablated.

There is a further risk that such an ablation can also adversely affect sensitive structures in the vicinity of the ablation area, e.g. nerves. Moreover, ablation is particularly difficult if a blood vessel is present in the vicinity of the ablation zone, which blood vessel dissipates heat and thus changes the thermal ablation volume. All these problems lead to the fact that ablation processes can to date only be controlled imprecisely.

SUMMARY

At least one embodiment of the present invention provides an actuation system for in particular automatically actuating an ablation instrument for an ablation process in a tissue volume, which actuation system ensures a more controlled ablation and a better predictability of the ablation result.

An inventive actuation system of at least one embodiment comprises at least:
  an input interface for image data of the tissue volume,
  an identification unit for identifying a target tissue using the image data,
  a model production unit for producing initial process models and/or fine process models of expected ablation developments, which is linked to a value derivation unit for deriving model measured values from an initial process model and/or to a value determination unit for determining measured values representing the ablation progress,
  a command derivation unit for deriving control commands on the basis of initial process models and/or for deriving refined control commands on the basis of fine process models,
  a comparator for comparing measured values and
  an instrument interface for transmitting control commands and/or refined control commands to the ablation instrument.

An inventive actuation method of at least one embodiment comprises at least:
a) identifying a target tissue using image data of the tissue volume acquired using an imaging system, b) generating an initial process model of an expected ablation development as a function of defined process parameters on the basis of stored ablation model data,
c) deriving expected initial model measured values from the initial process model,
d) generating initial control commands on the basis of the initial process model,
e) actuating the ablation instrument using the initial control commands,
f) determining measured values representing the ablation progress,
g) comparing the measured values with the initial model measured values,
h) generating a fine process model on the basis of the comparison and planning the further ablation progress on the basis of the fine process model and
i) deriving refined control commands on the basis of the fine process model which can subsequently be used for renewed actuation of the ablation instrument.

Thus, in an actuation method according to at least one embodiment of the invention, an initial process model of an expected ablation development is firstly generated on the basis of stored ablation model data. This can be, for example, ablation data based on experience obtained ex situ or in situ from preliminary examinations, or a computer simulation of the physical processes of RF energy coupling-in and thermal diffusion or of the progression of the icing. The ablation process is now planned on the basis of the initial process model in which expected initial model measured values are generated. They are used as the basis for initial control commands by which the ablation instrument is firstly actuated.

What follows then is a feedback of measured values from the ablation instrument into the actuation system. These measured values are compared to the initial model measured values from the initial process model. An iteration is undertaken which results in an evermore precise modeling process during the progression of the actuation method. The further actuation of the ablation instrument is effected on the basis of the refined control commands obtained from the iteration. The potential for refining the actuation method achieved in this manner automatically includes the fact that an ablation process controlled in this manner can be effected more safely and more quickly because care does not have to be taken to have progression simulation data which is as accurate as possible at the beginning of the process. Especially when combining an ablation with the operation of imaging systems such as computed tomography scanners, this results in a high potential for saving time and therefore costs, in particular if, as preferred, a completely automatic actuation is effected with the aid of the actuation system. By way of example, provision can also be made within the scope of such a fully automatic actuation for the ablation instrument itself to be automatically moveable, e.g. with the aid of robotic systems.

Therefore, as explained above, the actuation system according to at least one embodiment of the invention has units designed analogously to the actuation method, with, for example, the model production unit being able to be designed both as an independent generation unit for models and as an input interface linked to a database in which corresponding process models are stored. Analogously, both the value derivation unit for deriving model measured values and the value determination unit for determining measured values representing the ablation progress can be arranged both within the actuation system and externally, e.g. in the form of or in combination with corresponding databases which for example are called over the Internet or a local intranet. However, the value determination unit can also be designed in the form of a measured value input interface by means of which measured values are fed into the actuation system from outside of the actuation system.

Individual elements of the actuation system can serve a number of purposes within the scope of the actuation method according to at least one embodiment of the invention. Thus, for example, the model production unit can be used both for producing the initial process model and, subsequently, for producing refined fine process models. Likewise, the command derivation unit can be used to derive control commands on the basis of the initial process model and also to derive refined control commands on the basis of the fine process models.

The abovementioned interfaces do not necessarily have to be designed as hardware components but can also be implemented as software modules, for example if the image data can be taken from another component implemented on the same instrument, e.g. an image reconstruction device or the like, or only has to be transferred by software to this other component. Likewise, the interfaces can also be composed of hardware and software components, such as a standard hardware interface which is specifically configured for the particular use by software.

Overall, a majority of the components for implementing the actuation system in the fashion according to the invention, in particular the identification unit, the model production unit, the value derivation unit, the value determination unit, the command derivation unit and the comparator, can be implemented wholly or partly in the form of software modules on a processor.

It is for this reason that at least one embodiment of the invention also comprises a computer program product which is directly loadable into a processor of a programmable actuation system, with program code segments/modules for executing all steps of a method according to at least one embodiment of the invention if the program product is executed on the actuation system.

Further particularly advantageous refinements and developments of at least one embodiment of the invention also emerge from the dependent claims and the following description. Here, the actuation method according to at least one embodiment of the invention can also be developed according to the present claims of the actuation system, and vice versa.

Both the actuation system according to at least one embodiment of the invention and the actuation method according to at least one embodiment of the invention are mainly distinguished by the fact that a feedback of measured data from the ablation process into the actuation is made possible. Accordingly, it is particularly advantageous if iterative repetitions of the steps c) to i) occur in an actuation method according to at least one embodiment of the invention, with the lastly generated fine process model being used, i.e. being redefined, as the new initial process model in the iterative repetitions. This effects a successive refinement of the actuation method, which as a result is very finely matched to the tissue volume to be ablated toward the end of the ablation process.

Thus, it is not mandatory to use very precise ablation model data as input data, but in principle it suffices to use the currently known, abovementioned model data, originating e.g. from ex situ preliminary examinations. During the progress of the actuation method, the actuation system anyway obtains sufficient feedback about the actual ablation progress and so the ablation model data only acts as initial values which are then continuously verified during the progress of the method. Hence, the actuation system is self-learning—measured data obtained from the ablation progress can even be used for forming a refined model and so already refined ablation model data can be stored for subsequent ablation processes.

Such an iterative approach additionally has the advantage that a closed control circuit is created. If components of the actuation system or of the ablation instrument fail, this circuit is interrupted and so such errors are very easily detectable.

Preferably, an actuation system according to at least one embodiment of the invention has a differentiator which is designed such that in the image data it distinguishes between at least two of the following tissue volumes:
ablation volume,
non-ablation volume,
volume at risk,
vessel volume.

Thus, the differentiator distinguishes between different tissue volumes, with the ablation volume preferably being one of these tissue volumes and the non-ablation volume, the volume at risk and the vessel volume respectively being distinguished from the ablation volume. Here, a non-ablation volume is intended to be understood to be the tissue area which lies outside of the ablation volume. That volume which can lead to a damage of bodily functions in the case of inadvertent ablation constitutes a volume at risk. Vessel volumes are mainly volumes of blood and lymph vessels. As already explained above in the introduction, it is essential that the ablation volume is distinguished from the other three volumes during an ablation: The non-ablation volume should not be ablated as far as possible, the volume at risk, as a subset of the volume of the non-ablation volume, should not be ablated under any circumstances and the vessel volume contributes to heat dissipation which can influence the ablation process in the ablation volume. Thus, taking into account these different volumes using the differentiator constitutes a particular refinement of the actuation method according to at least one embodiment of the invention.

Furthermore, the actuation system according to at least one embodiment of the invention preferably has a remaining area determination unit which is designed such that it determines a remaining area of the target tissue which remains after performing an ablation on the basis of the initial control commands. Using the remaining area determination unit, it is possible to determine which non-ablated area of the target tissue, in particular the percentage thereof, the volume thereof in absolute figures and the position thereof, remains in the tissue volume after performing an ablation on the basis of the initial control commands. Here, what should be taken into account is that, within the scope of the iteration, it is always those control commands which are defined as initial control commands which are used as input control commands in the step d) of the actuation method in the respective iteration cycle. This means that even with the method in progress, a refinement of the estimate of the remaining area is possible.

By way of example, in the case of semi-automatic ablation processes, knowledge of the respective remaining area assists an operator with the decisions as to which ablation instrument, which ablation method, which ablation duration and which ablation locations are selected for his ablation. Likewise, the information regarding the remaining area of the target tissue can be used by the actuation system itself—for example in the case of a fully automatic ablation process—in order to optimize the initial control commands.

MUM An actuation system according to at least one embodiment of the invention also preferably has a definition data input interface for accepting definition data relating to tissue volumes. Here, definition data is understood to be that data which comprises information relating to the type or use of a certain tissue volume, such as the definition that a certain tissue volume is a volume to be ablated or not to be ablated. By way of example, a specific tissue volume of this type can thus be defined via the input interface using a database or an image detection system, or by manual input. That is to say the corresponding tissue volume can be marked, with it being possible for the definition data to be particularly accurate and fine due to the logic of the image detection system and/or the criteria of the database.

Furthermore, it is particularly advantageous if an actuation system according to at least one embodiment of the invention has an ablation instrument selection unit which selects from the image data a possible ablation instrument which is as optimal as possible, taking the target tissue into account. Depending on the respective target tissue, the ablation instrument selection unit can be used to select that ablation instrument from a number of different ablation instruments which is optimally equipped for the ablation of the respective target tissue. To this end, use can be made, either fully automatically or with the aid of manual inputs, of corresponding characteristics of the respectively available ablation instruments.

The characteristics comprise, for example, a type identifier of the ablation instrument, the technical data thereof such as maximum power and the like, the geometry of the applicator thereof, i.e. of the ablation tip or needle thereof, the dimensions of the active zone of the applicator thereof or specifications relating to the geometry of the possible spatial coverage of the applicator thereof (e.g. the reach of the needles and the expected shape of the ablation volume). Thus, for example, a selection can be made between a bipolar and a unipolar ablation instrument, or between ablation instruments with different powers. Furthermore, the optimum ablation probe can be determined for a given ablation instrument (for example from a number of ablation probes with different umbrella diameters). The ablation instrument selection unit can also be used for monitoring whether the ablation instrument, selected in advance by e.g. an operator, which was connected to the actuation system is correct.

It is particularly preferable for the actuation system according to at least one embodiment of the invention to have a registration unit for registering a plurality of successively determined image data to each other. Here, a registration is understood to mean that image data of the same volume area or at least similar volume areas are brought into best-possible correspondence with one another. During the actuation method, successive further image data can be fed into the actuation system from the imaging system. Using an appropriate registration unit, these image data are related to one another such that a user and the actuation system according to at least one embodiment of the invention itself obtain a solid basis for evaluating the respective ablation situation.

Furthermore, the actuation system can preferably have a characteristics input interface for characteristics of ablation instruments and a characteristics processing unit which supplies the model production unit with model ablation parameter values derived from the characteristics of an ablation instrument. Here it is possible for the characteristics processing unit to be linked optionally to a database (within or external to the actuation system) from which the characteristics of the respective ablation instrument can be obtained. That is to say characteristics of different ablation instruments, such as the power, the size, the number of the ablation probes and many more, enter the actuation system via the characteristics input interface, which actuation system thus obtains a valid basis for respectively selecting the right ablation instruments. However, type identifiers such as an identification number of the ablation instrument can also be used as characteristics, with all further characteristics in turn being able to be identified on the basis of this from an internal or external database.

A particularly advantageous embodiment of the actuation system comprises a visualization output interface for transferring visualization data to a visualization medium for visualizing the initial process model and/or the fine process model together with the target tissue. This output interface can be used to convey an image to an operator using the visualization medium, e.g. a monitor or a printer, which image shows approximately how an ablation process is progressing in the target area or what results it is yielding. This can be illustrated both initially for the initial process model and in the further progression of the ablation process on the basis of the fine process models. Thus, an evermore reliable image of what is happening in the ablation process on the basis of the respective control commands is obtained during the progression of the ablation. By way of example, the temperature distribution in the tissue can be visualized by appropriate coloring in of the displayed tissue images.

Finally an actuation system according to at least one embodiment of the invention preferably has an interface for acquiring and/or transmitting coordinates from and/or to a navigation system. Such a navigation system can for example be coupled to both the ablation instrument and the imaging system such that an operator or the actuation system is provided with orientation during the ablation process.

Within the scope of the actuation method according to at least one embodiment of the invention, the image data is preferably obtained from a tomography scan running in parallel. This is understood to mean a prompt or simultaneous acquisition of tomography raw image data which is effected within the temporal scope of the ablation process. Thus, for example, this can firstly be effected before performing an ablation and then after performing first ablation steps and finally after the ablation process has been completed, or simultaneously with or in equal intervals during the ablation process. This makes it possible for the image data to be respectively fed from the tomography scan into the actuation method according to at least one embodiment of the invention as additional input parameters and further refine said actuation method.

The image data from the progressing tomography scan can within the scope thereof be evaluated as a type of measured value for the iteration of the actuation method. In the process, it can depend on with which method the image data is acquired and on which ablation method is selected: For example, magnetic resonance images clearly show a thermal distribution in heat treatment or cryotherapy. Computed tomography images for example clearly show the icing zone in the cryoablation.

The defined process parameters can both be defined in advance and only be defined within the scope of the actuation method. They particularly preferably comprise control-specific process parameters which can comprise the following parameters:
  type of ablation energy influx,
  duration of ablation energy influx,
  location of ablation energy influx,
  spatial ablation energy influx progression,
  temporal ablation energy influx progression and
  number of ablation energy influxes.

Generating the initial process model as a function of control-specific process parameters, which can comprise the listed parameters but can also go beyond them, is advantageous, inter alia, in that the effects which can be created by operating an ablation instrument by the actuation system can be taken into account in the model. Thus, by way of example, what happens if the energy were to be inserted at a different energy influx location or if the ablation energy were to be increased or decreased is determined.

The process parameters preferably also comprise instrument-specific process parameters which can comprise the following parameters:
  number of ablation energy influx probes and
  type of ablation energy influx probes.

Modeling the initial process model as a function of instrument-specific process parameters, which again can comprise those listed above, inter alia advantageously brings about that the system is able to distinguish or select between different ablation instruments.

The process parameters preferably also comprise tissue-specific process parameters which can comprise the following parameters:
  a value for the heat conduction of the target tissue and/or of the tissue in the vicinity of the target tissue,
  a heat dissipation factor of vessels within the tissue,
  an ablation coefficient representing the ablation property of the tissue and
  a heat absorption coefficient representing in each case globally, partly or distinguished locally the absorption property of the tissue.

Forming a model of the ablation process taking into account tissue-specific process parameters is advantageous in that, inter alia, the process can be optimized in a targeted fashion for certain types of tissue, e.g. different organs such as liver, kidney or spleen. Additionally, the use of tissue-specific process parameters can also take into account that a tissue has different internal structures.

The measured values particularly preferably comprise temperature values and/or impedance values. With the aid of these measured values, which can these days already be determined directly in situ by the ablation instrument, reliable data can be used in the actuation method as measured values for the iteration which, as characteristic variables, are already common these days. As indicated previously, the measured values can also comprise different information, preferably ablation information generated from image data.

Furthermore, the measured values particularly preferably comprise position information of the ablation instrument. With the aid thereof it is possible for the location of the ablation energy influx to be determined during the ablation method or in the run-up thereto, and hence the exact positioning of the energy can be ensured.

BRIEF DESCRIPTION OF THE DRAWINGS

In the following text, the invention is once again explained in more detail on the basis of example embodiments with reference to the attached figures. Here, the same components in the various figures are provided with identical reference symbols, in which FIG. 4 shows a schematic block diagram of an example embodiment of an actuation system according to the invention and FIG. 5 shows a schematic block diagram of an example embodiment of an actuation method according to the invention.

DETAILED DESCRIPTION OF THE EXAMPLE EMBODIMENTS

Figure 1:
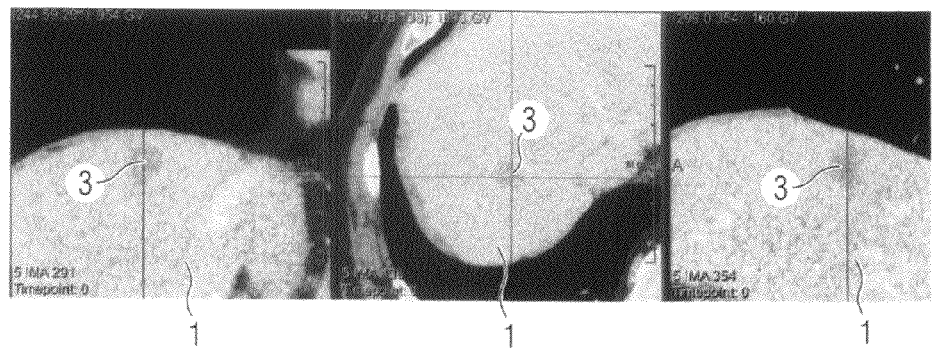
FIG. 1 shows a view of a hepatic tumor in hepatic tissue from different slice image perspectives, obtained within the scope of a computed tomography scan.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

WMA Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a tissue volume 1, in this case a human liver, in different slice perspectives of a CT image data record. Within the scope of the computed tomography method it is already possible to recognize a target tissue 3, in this case a hepatic tumor, and display the latter in a contrasted fashion.

Figure 2:
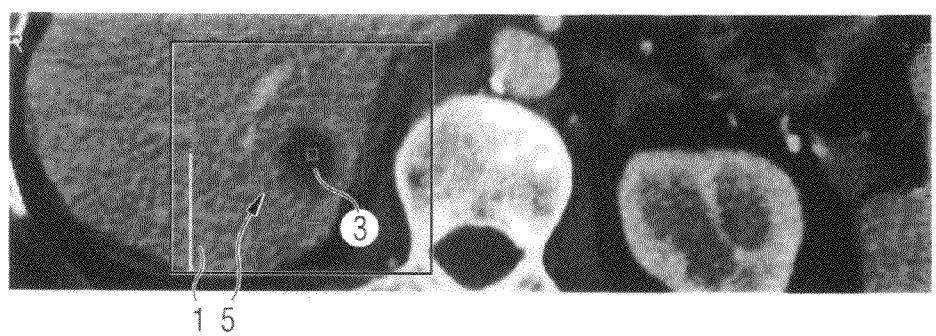
FIG. 2 shows a post-processed image data record of the hepatic tumor from FIG. 1 in a further slice image perspective.

FIG. 2 shows the same hepatic tumor 3 in a further slice perspective. In the run-up to the actuation method according to the invention, it is possible for the tumor area of the hepatic tumor 3 and, additionally, a so-called safety margin 5 to be defined, for example using recognition software or by manual input by a user. By way of example, a safety margin 5 of one centimeter means that tissue up to a distance of one centimeter from the tumor boundary is also intended to be destroyed.

In the method according to an embodiment of the invention, a user or a fully automatic actuation system or functional units combined with an actuation system can optionally also detect or define structures at risk and vessels. To this end a user can, for example, point into a vessel within the image data using a computer mouse and thus start a recognition or definition algorithm. Likewise said user can use the mouse pointer to directly encircle and thus mark sensitive structures at risk. By contrast, automatic recognition and definition systems feed definition data into the actuation system on the basis of recognition algorithms and/or database entries.

Figure 3:
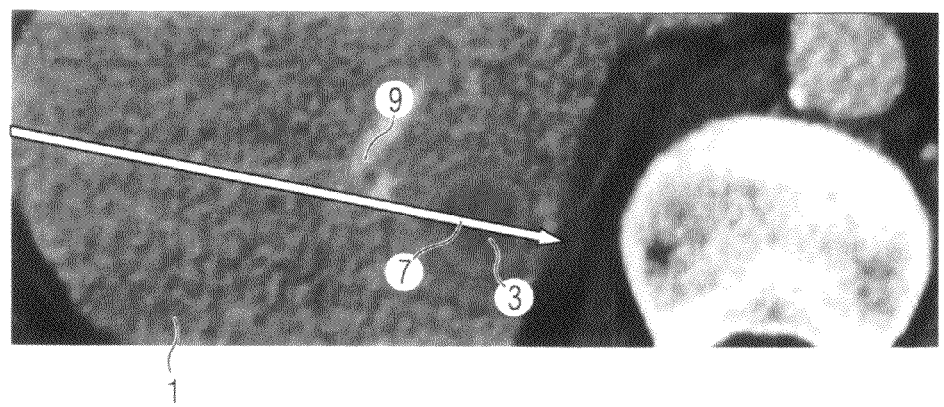
FIG. 3 shows a detailed view from FIG. 2 with a simulated needle and a simulated ablation heat distribution.

Subsequently, in an actuation method according to an embodiment of the invention, an initial process model is generated, that is to say a simulation is performed. On the basis of a detailed view of the illustration from FIG. 2, FIG. 3 shows how image processing for a user works within the scope of such a simulation: The hepatic tumor 3 and the surrounding tissue of the liver 1 are illustrated in colors which differ from one another. Likewise, a blood vessel 9 is extracted from the image data and displayed in a different color. Around the liver tumor 3, a heat distribution is illustrated in color, again using colored contours, approximately in the style of a topographic map. Furthermore, a simulation of a needle 7 of an ablation instrument is illustrated. The illustrations of the simulated heat distribution in the illustrated image differ as a function of the position of the needle and further ablation parameters which respectively depend on the selected ablation instrument. That is to say the simulation is performed as a function of the tissue, the ablation instrument and of the handling of the ablation instrument by an actuation system or—in the case of a semi-automatic actuation—by an operator.

Using such a simulation in advance, the operator is conveyed an impression as to approximately how an ablation progresses on the basis of the data input available prior to the start of the ablation. Using the image data illustrated in FIG. 3, an operator or an automatic system can position the ablation instrument such that the needle thereof is, in an ideal case, precisely located at the location of where the simulated needle is positioned as well. Navigating the needle is preferably performed whilst being monitored on an image with the aid of the imaging system, for example with the aid of fluoroscopy in the case of a CT or with short single scans to verify the position of the needle. If the needle has been positioned correctly, their individual pole antennas are possibly still deployed and a final quick scan is preferably performed by the imaging system for monitoring.

The ablation process can now be started on the basis of this scan which is adjusted by registration with previous scans: Initial control commands are generated and the initial process model can once again be output to an operator for confirmation. Alternatively the actuation system can also start the process automatically.

FIG. 4 shows a schematic block diagram of an example embodiment of an actuation system 11 according to the invention with an input interface 13 for image data BD, an instrument interface 27 for passing on control commands SB or refined control commands VSB to an ablation instrument 29, an underlying data input interface 35, a characteristics input interface 41, a visualization output interface 45 and a navigation interface 47.

Arranged between these interfaces are an identification unit 15, a model production unit 17 linked to a model database MDB, a value derivation unit 19, a command derivation unit 21, a value determination unit 23 and a comparator 25 and, furthermore, a differentiator 31, a remaining area determination unit 33, an ablation instrument selection unit 37, a registration unit 39 and a characteristics processing unit 43. The actuation system 11 and the ablation instrument 29 are connected via radio link to a navigation system 49. To this end, the ablation instrument 29 has—analogously to the navigation interface 47 of the actuation system 11—a radio interface 50.

The components illustrated within the actuation system 11 (with the exception of the navigation interface 47) in the block diagram are designed in the form of software-controlled modules within a processor.

Image data BD from an imaging system, for example from a computed tomography scanner, reaches the identification unit 15 via the input interface 13. Additionally, the differentiator 31 distinguishes between different tissue volumes in the image data BD, specifically between an ablation volume, a non-ablation volume, a volume at risk and a vessel volume. In the identification unit 15, a target tissue 3 is identified in the image data BD. Additionally, definition data DD is fed into the identification unit 15 via the underlying data input interface 35. The registration unit 39 is used to register image data BD of different origin to one another; specifically image data successively determined one after the other. As a result, processed tissue data AGD relating to the target tissue 1 and possibly tissue volumes adjacent to the target tissue 1 is available in the identification unit 15, which processed tissue data AGD is necessary as a basis for a targeted ablation of the target tissue.

A second central component of the actuation system 11 is the model production unit 17. It produces process models of expected ablation processes in the target tissue 1, in particular an initial process model PM and at least one refined fine process model FPM. To this end, it is supplied with data from the model database MDB, the characteristics processing unit 43, the ablation instrument selection unit 37, and the value derivation unit 19 or the value determination unit 23. The model production unit selects fitting process models from the model database MDB as a function of the input of the other units linked thereto. In the process, the value derivation unit 19 derives different initial model measured values MM depending on the selected initial process model while the value determination unit 23 feeds actual measured values MW into the model production unit 17. Here, the initial model measured values MM are selected such that they are comparable to the actual measured values MW, that is to say that they are based on the same parameters or on different parameters which can nevertheless be derived from one another such that they can be brought into line with one another. The characteristics processing unit 43 obtains characteristics KD of an ablation instrument 29 via the characteristics input interface 41, from which characteristics said characteristics processing unit derives model ablation parameter values MAW which are also used as input for the model production unit 17, just like selection data SD from the ablation instrument selection unit 37, which selects a suitable ablation instrument 29 for the subsequent ablation as a function of the image data BD.

Thus, the main input for the model production unit 17 are the processed tissue data AGD, the information SD, MAW relating to the ablation instrument 29 and virtual or actual measured values MM, MW which depend on a selected initial process model or which are determined during an ablation process.

First of all an initial process model PM and later, during the process, fine process models FPM are passed on, as a function of said input data, to the command derivation unit 21 which derives control commands SB from the initial process model PM and derives refined control commands VSB from the fine process models FPM, and said command derivation unit passes these on via the instrument interface 27 to the ablation instrument 29 in order to control the latter.

The ablation instrument 29 performs an ablation on the basis of the control commands SB and generates measured values MW which are again fed into the actuation system 11 via the value determination unit 23. The value determination unit 23 communicates with the comparator 25 which generates measured value comparison data MWV from the measured values MW and the model measured values MM from the value derivation unit 19. This measured value comparison data MWV, together with the measured values MW, in turn serves as input for the model production unit 17, which derives a fine process model FPM therefrom.

This fine process model is in turn fed into the command derivation unit 21 which derives refined control data VSB for controlling the ablation instrument 29 in the manner described above on the basis of the fine process model.

In addition to the previously described functions of the actuation system 11, provision is made for passing on visualization data VD to a visualization medium, e.g. a display monitor, via the visualization output interface 45. As a result of this, e.g. the target tissue 1 together with the respectively active process model can be illustrated visually for an operator, as a result of which the ablation process becomes comprehendible to him. Furthermore, communication with a navigation system 49 can be established via the navigation interface 47 and the radio interface 50 of the ablation instrument 29, on the basis of which the ablation instrument 29 can be located and a comparison with the measured values can be effected.

It can be seen that by using very different input interfaces, sources of information and visualization possibilities, an initial process model PM is first of all generated using the actuation system 11, which initial process model is in turn refined by iteration, that is to say by feedback of the measured values MW, from the ablation instrument 29. This process can iteratively progress a number of times such that the data basis for the actuation within the scope of the actuation method according to the invention is evermore refined and hence an optimal ablation result is achievable.

FIG. 5 schematically shows an actuation method according to an embodiment of the invention in a block diagram. It comprises identifying ID a target tissue 3 from image data BD of a tissue volume 1 acquired using an imaging system. That is followed by generating IPMG an initial process model PM of an expected ablation development as a function of defined and/or definable process parameters on the basis of stored ablation model data.

Thereafter this is followed by deriving IMMA expected initial model measured values MM from the initial process model PM and then by generating ISBG initial control commands SB on the basis of the initial process model PM. The ablation instrument 29 is actuated in an actuation AS using these initial control commands SB. Determining MWE measured values MW representing the ablation progress and comparing VMW the measured values MW with the initial model measured values MM serves for generating FPMG a refined fine process model FPM and planning the further ablation progress on the basis of the fine process model FPM. From this, refined control commands VSB are derived in turn in a derivation VSBG on the basis of the fine process model FPM.

The refined fine process model FPM can be redefined in the iterative process, in turn fed in as initial process model PM, and serve as an input model for a renewed derivation IMMA. A closed loop is created which is only terminated by the end of the ablation process.

Once the ablation process is finished, it is possible to perform a tomography scan for evaluation, preferably supported by a contrast agent. The necrotic zone—that is to say the ablated tissue—for example appears to be darker in the computed tomography image. This makes it possible to recognize whether a target tissue was completely ablated.

This recognition is relevant in a number of aspects: For example, if the target tissue together with the safety margin was not completely acquired or could not be completely acquired, a new ablation could be performed after a certain amount of time. In such a case, the result of the final tomography scan can be used as initial data for a subsequent additional ablation. Also, such information can also be used to refine the model in order to make a statement on the quality of the ablation which has just been performed and thus, indirectly, on the actuation system or actuation method according to an embodiment of the invention.

The evaluation of the ablation success is also simplified indirectly with the aid of the actuation method according to an embodiment of the invention: Since the tomography scan before an ablation and thereafter are usually not precisely congruent, i.e. the original target tissue and the current necrosis are not exactly in the same place, it is in itself difficult to precisely evaluate or even quantify the ablation success. Here the measured data collected during the ablation could be used to output a forecast as to with what probability the entire volume was acquired.

Finally, reference is once again made to the fact that the actuation method described above in detail and the illustrated actuation system are only example embodiments which can be modified by a person skilled in the art in a number of ways without leaving the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An actuation system for an ablation instrument for an ablation process in a tissue volume, comprising:
    an input interface configured to receive image data of the tissue volume;
    a processor configured to implement:
        an identification unit configured to identify a target tissue of a patient using the image data;
        a model production unit configured to produce an initial process model of expected ablation developments in the target tissue, the model production unit being linked to a value derivation unit configured to derive model measured values from the initial process model;
        a command derivation unit configured to derive initial control commands on the basis of the produced initial process model; and
        a value determination unit configured to determine measured values representing ablation progress after using the initial control commands;
    an instrument interface configured to transmit the initial control commands to the ablation instrument; and
    a comparator configured to compare the measured values with the model measured values,
        the model production unit being further configured to produce a refined process model of expected ablation developments in the target tissue as a volume of the target tissue chancres due to implementation of a previous process model based on a comparison of the measured values representing the ablation progress in the target tissue with the previous process model, the model production unit being further configured to plan further ablation of the target tissue on the basis of the produced refined process model,
        the command derivation unit further configured to derive refined control commands on the basis of the produced refined process models, and
        the instrument interface configured to transmit refined control commands to the ablation instrument.

2. The actuation system as claimed in claim 1, further comprising a differentiator, configured to, in the image data, distinguish between at least two of the following tissue volumes: ablation volume, non-ablation volume, volume at risk, and vessel volume.

3. The actuation system as claimed in claim 1, wherein the is further configured to implement a remaining area determination unit, configured to determine a remaining area of the target tissue which remains after performing an ablation on the basis of the initial control commands.

4. The actuation system as claimed in claim 1, further comprising a definition data input interface configured to accept definition data relating to tissue volumes.

5. The actuation system as claimed in claim 1, wherein the processor is further configured to implement an ablation instrument selection unit configured to select from the image data a possible ablation instrument, taking the target tissue into account.

6. The actuation system as claimed in claim 1, wherein the processor is further configured to implement a registration unit configured to register a plurality of successively determined image data to each other.

7. The actuation system as claimed in claim 1, further comprising:
    a characteristics input interface configured to accept characteristics of ablation instruments; wherein
    the processor is further configured to implement a characteristics processing unit configured to supply the model production unit with model ablation parameter values derived from characteristics of an ablation instrument.

8. The actuation system as claimed in claim 1, further comprising a visualization output interface configured to transfer visualization data to a visualization medium, the visualization medium configured to visualize at least one of the initial process model and the refined process model together with the target tissue.

9. The actuation system as claimed in claim 1, further comprising a navigation interface configured to at least one of acquire and transmit coordinates at least one of from and to a navigation system.

10. The actuation system as claimed in claim 1, wherein the value determination unit is further configured to determine measured values representing the ablation process after the refined control commands.

11. The actuation system as claimed in claim 1, wherein the actuation system is further configured to actuate the ablation instrument fully automatically.

* * * * *